(12) United States Patent
Haaland

(10) Patent No.: US 11,679,084 B2
(45) Date of Patent: Jun. 20, 2023

(54) METHOD AND COMPOSITIONS FOR RENDERING OPIOIDS SAFE

(71) Applicant: NOPIOID, LLC, Fraser, CO (US)

(72) Inventor: Peter Haaland, Belmont, MA (US)

(73) Assignee: NOPIOID, LLC, Fraser, CO (US)

(*) Notice: Subject to any disclaimer, the term of this patent is extended or adjusted under 35 U.S.C. 154(b) by 116 days.

(21) Appl. No.: 16/988,881

(22) Filed: Aug. 10, 2020

(65) Prior Publication Data

US 2021/0038522 A1 Feb. 11, 2021

Related U.S. Application Data

(60) Provisional application No. 62/885,049, filed on Aug. 9, 2019.

(51) Int. Cl.
| | | |
|---|---|---|
| *A61K 9/20* | (2006.01) | |
| *A61K 31/4468* | (2006.01) | |
| *A61K 31/485* | (2006.01) | |
| *A61K 31/451* | (2006.01) | |
| *A61K 31/137* | (2006.01) | |
| *A62D 3/38* | (2007.01) | |
| *A62D 101/26* | (2007.01) | |

(52) U.S. Cl.
CPC .......... *A61K 9/2013* (2013.01); *A61K 31/137* (2013.01); *A61K 31/4468* (2013.01); *A61K 31/451* (2013.01); *A61K 31/485* (2013.01); *A62D 3/38* (2013.01); *A62D 2101/26* (2013.01)

(58) Field of Classification Search
CPC ........ A62D 3/40; A62D 2101/28; A62D 3/38; A62D 2101/26; A62D 2203/04; B09B 5/00; B09B 3/0075; A61K 31/4468; A61K 9/2013; A61K 31/137; A61K 31/485; A61K 31/451
See application file for complete search history.

(56) References Cited

U.S. PATENT DOCUMENTS

| | | | |
|---|---|---|---|
| 8,981,175 B2 | 3/2015 | Stalons | |
| 2009/0180936 A1 | 7/2009 | Anderson et al. | |
| 2015/0265867 A1* | 9/2015 | Sarangapani | .......... B65D 81/02 428/34.1 |
| 2016/0184621 A1 | 6/2016 | Schug et al. | |

FOREIGN PATENT DOCUMENTS

| | | | | |
|---|---|---|---|---|
| DE | 102006047270 A1 * | 4/2008 | ................ | A61J 3/00 |
| DE | 102006047270 A1 | 4/2008 | | |
| WO | 2008040512 A2 | 4/2008 | | |

OTHER PUBLICATIONS

Gao et al., "Evaluation of an activated carbon-based deactivation system for the disposal of highly abused opioid medications", Drug Development and Industrial Pharmacy, vol. 44, No. 1, 2018, pp. 125-134.

(Continued)

*Primary Examiner* — Jianfeng Song
(74) *Attorney, Agent, or Firm* — Michael Best & Friedrich LLP

(57) ABSTRACT

Exemplary compositions, methods, systems, and kits are disclosed that render excess pharmaceuticals safe by chemically transforming the active pharmaceutical ingredient into an environmentally benign and biologically inert form. The methods and kits have additional advantages of convenience, low cost, long shelf life, and ease of handling.

10 Claims, 18 Drawing Sheets

Oxycodone

Oxycodone-N-oxide fentanyl

Diastereomers of fentanyl-N-oxide

(56) References Cited

OTHER PUBLICATIONS

Kadajji et al., "Water Soluble Polymers for Pharmaceutical Applications", Polymers, vol. 3, 2011, pp. 1972-2009.
Kok et al., "N-Demethylation of N-methyl alkaloids with ferrocene", Bioorganic and Medicinal Chemistry Letters, vol. 20, 2010, pp. 4499-4502.
Waybright et al., "Validated Multi-Drug Determination using Liquid Chromatography-Tandem Mass Spectrometry for Evaluation of a Commercial Drug Disposal Product", J. Sep Sci., vol. 39, No. 9, 2016, pp. 1666-1674.
Deterra System, Drug Deactivation System, <www.deterrasystem.com>, webpage publicly available at least as early as Feb. 2015, 11 pages.
International Search Authority Invitation to Pay Additional Fees for Application No. PCT/US2020/045518 dated Nov. 19, 2020 (13 pages).
International Search Report and Written Opinion for Application No. PCT/US2020/045518 dated Jan. 18, 2021 (18 pages).

* cited by examiner nonanoyloxybenzene sulphonate (NOBS)

(triethylammoniomethyl)benzoyl] caprolactam chloride tetra-acetylethylenediamine (TAED)

METHOD AND COMPOSITIONS FOR RENDERING OPIOIDS SAFE

RELATED APPLICATIONS

This application claims priority to U.S. Provisional Application No. 62/885,049, filed Aug. 9, 2019, which is hereby incorporated by reference in its entirety.

TECHNICAL FIELD

The present disclosure relates generally to conveniently rendering prescription medicines safe for disposal in wastewater or landfills.

BACKGROUND

The diversion of controlled pharmaceutical substances from their prescribed uses has emerged as an important factor in poisoning and addiction. It is a pernicious threat to public health and the environment. Despite government regulations requiring that unused prescriptions be disposed of to avoid these externalities, the public's compliance with requirements to return unused medicines to police stations, pharmacies, or hospitals is abysmal. A safe and effective method for disposal of these pharmaceutical compositions is needed.

Schug et al. (U.S. application Ser. No. 15/058,321) discloses a disposal method for pharmaceuticals comprised of an acid and activated carbon. A deficiency of the method according to Shug is that pharmaceutical compositions are generally not chemically decomposed by acid—they must survive digestion in the human stomach at pH-2. A second deficiency of this method is that the active pharmaceutical ingredient is physisorbed, in other words reversibly bound, to the carbon. This results in an equilibrium being established between the bound and free forms of the compound, so that release of the active pharmaceutical ingredient occurs by diffusion when discarded into a landfill or wastewater. Moreover, the capacity of the adsorptive carbon saturates when excess adsorbate is present causing incomplete segregation of the active pharmaceutical ingredient. Evidence of these deficiencies is documented in Xinyi Gao, Pooja Bakshi, Sindhu Sunkara Ganti, Mahima Manian, Andrew Korey, William Fowler & Ajay Banga (2018), *Evaluation of an activated carbon-based deactivation system for the disposal of highly abused opioid medications*, Drug Development and industrial Pharmacy, 44:1, 125-134, and Waybright, Ma, and Schug, *Validated multi-drug determination using liquid chromatography with tandem mass spectrometry for the evaluation of a commercial drug disposal product* J Sep Sci. 2016 May; 39(9): 1666-74.

Another deficiency of prior art methods based on activated carbon is illustrated by the Deterra product (www.deterra.com). These products produce solid waste including a plastic pouch and insoluble, solid, sorbent coating. The price of these systems is high—between $0.23 and $1.00 per opioid pill—constraining application of the method at the scale of the global problem of prescription drug diversion.

The prior art method of central site incineration requires transporting, securing, and handling larger collections of hazardous materials. Beyond the logistical and compliance limitations, this is especially problematic in the case of some potent opioids, such as of carfentanyl, where minimal dermal or inhaled doses can be toxic to personnel that aggregate and handle the materials.

For these and other reasons described below, there is a compelling need for a convenient and scalable method of irreversibly rendering pharmaceutical compounds safe for disposal.

SUMMARY OF THE INVENTION

The present disclosure provides compositions, methods, systems, and kits to chemically transform pharmaceutical compounds so that they may be safely discarded in wastewater or landfills.

An exemplary embodiment for rendering oxycodone tablets safe adds a tablet comprised of sodium percarbonate, tetraacetylethylenediamine (TAED), and water to a prescription vial with unused prescription tablets. The size and composition of the tablet is chosen to ensure complete oxidation of the active pharmaceutical ingredients to oxycodone-N-oxide, which has no pharmacological activity and is a standard metabolite that humans excrete in their urine after consuming oxycodone. The mixture may optionally be shaken and remains concentrated in the vial for at least twenty minutes at room temperature, after which the N-oxide may be discarded in wastewater and the plastic vial may be recycled.

A second embodiment for rendering opioid tablets safe adds a powder comprised only of sodium perborate and water at a temperature above 60° C. to the prescription vial. The mixture may optionally be started with room temperature water and heated to above 60° C. in a microwave oven. In either case, the kinetics of deactivation is accelerated at these temperatures, and the resulting oxycodone N-oxide may be safely discarded.

A third embodiment for rendering fentanyl powder or tablets safe involves adding 3-chloro-peroxybenzoic acid (m-CPBA) and approximately 1:1 isopropyl alcohol and water to oxycodone tablets. The mixture may optionally be shaken to encourage dissolution of the tablets and allowed to react in the vial for ten minutes, after which it is safe to release to the environment.

As further described below, the use of a peroxide-based oxidizer such as sodium perborate, sodium percarbonate, acetyl peroxide, or m-CPBA oxidizes the piperidine ring in any opioid including oxycodone, hydrocodone, fentanyl, hydromorphone, morphine, heroin, and the like.

A fourth embodiment exploits dissolution aids to enhance the release of the active pharmaceutical ingredient from the prescription tablet excipients and coatings. These excipients include starches, stearates, cellulose, simple sugars, and sweeteners, while dissolution aids include enzymes, detergents, surfactants, abrasive materials, pH buffers, and the like whose composition may be tailored to specific tablet formulations.

BRIEF DESCRIPTION OF THE DRAWINGS

Certain aspects will become apparent and more readily appreciated from the following description of non-limiting exemplary embodiments, taken in conjunction with the accompanying drawings in which.

DETAILED DESCRIPTION OF THE INVENTION

1. Definition of Terms

Figure 1:
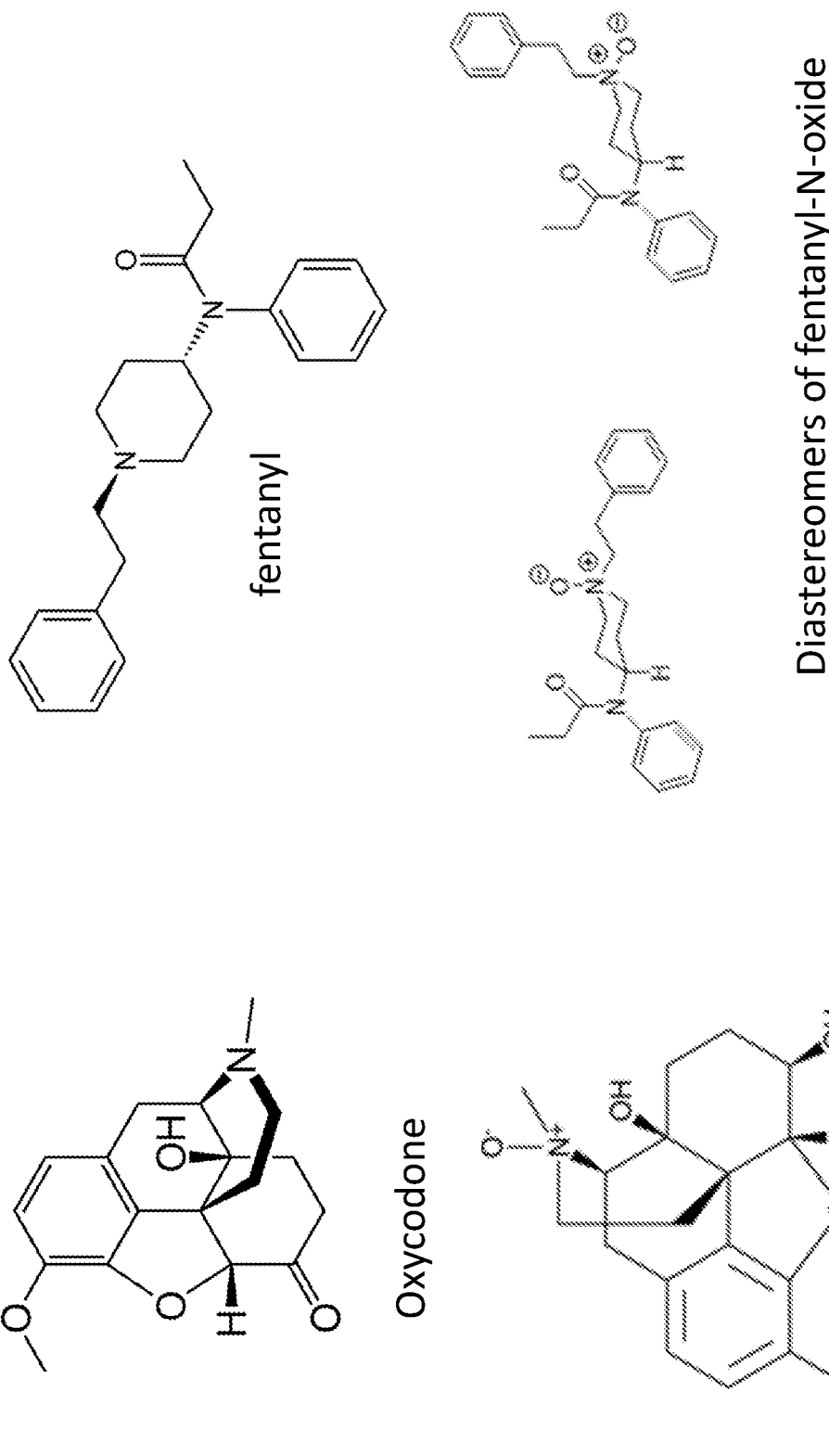
FIG. 1 is a chemical structure of oxycodone free-base, oxycodone-N-oxide, fentanyl, and diastereomers of fentanyl-N-oxide; the water-soluble acid form of oxycodone is protonated at the nitrogen atom.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of embodiments of the present disclosure. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . , and N, that is to say, any combination of one or more of the elements A, B, . . . , or N including any one element alone or in combination with one or more of the other elements which may also include, in combination, additional elements not listed.

The terms "first," "second," "third," and the like, as used herein, do not denote any order, quantity, or importance, but rather are used to distinguish one element from another.

The term "substantially," as used herein, represents the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The term "opioid," as used herein, represents a tablet, powder, or liquid that contains one or more of the alkaloids that bind opioid receptors in the central nervous system; examples include codeine, oxycodone, morphine, hydromorphone, fentanyl, heroin, bupranorphine, tramadol, and carfentanil.

The term "benzodiazepine," as used herein, is a biologically active molecule based on the fusion of a benzene ring and a diazepine ring.

The term "amphetamine," as used herein, is a pharmaceutical composition containing a phenylpropyl amine group.

The term "derivative" as used herein refers to pharmaceutical compounds that differ from the parent or reference compound, or class of compounds, by the arrangement or identity of structural components that do not affect the general type of pharmaceutical activity possessed by the parent or reference compound, or class of compounds (e.g., analogs, homologs). Derivatives possess the same general type of pharmaceutical activity as the parent or reference compound, or class of compounds. Specific examples of derivatives are found in FIGS. 11 and 12.

The term "prescription medicine," as used herein, represents a controlled substance whose purchase requires the approval of a physician or a license from a drug regulating governmental authority, such as the US Drug Enforcement Agency.

The term "excipient," as used herein, represents an inactive substance that serves as a vehicle or medium for a drug or other active pharmaceutical ingredient.

The term "accelerant," as used herein, represents molecules that react with oxidizers to produce organic peroxides that subsequently react with substrates at accelerated rates.

2. Description of Embodiments

Prescription medicines are dispensed as pharmaceutical dosage forms in the form of solid dosage forms (e.g., powders, tablets, capsules, granules), semi-solid dosage forms (e.g., soft gel), or liquid dosage forms (e.g., aqueous, lipid, oily or other solutions, emulsions such as oil-in-water emulsions, liposomes, aqueous or oily suspensions, syrups, elixirs) that contain active pharmaceutical ingredients (APIs) combined with excipients that facilitate dosing to patients. The solid dosage forms of tablets, dragees, capsules, pills, and granules can be prepared with coatings and shells such as enteric coatings and other coatings well known in the pharmaceutical formulating art. In such solid dosage forms the active compound may be admixed with at least one inert diluent such as sucrose, lactose or starch. They may optionally contain pacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin.

Granules typically comprise a disclosed compound, and preferably glidants such as silicon dioxide to improve flow characteristics. Implants can be of the biodegradable or the non-biodegradable type.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include an API and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

The amount of the carrier employed in conjunction with an API is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

Excipients are generally recognized as safe to consume and facilitate release of an API into the patient's body after injection, inhalation, or ingestion. Common excipients serve as binders, diluents, antifoaming agents, chelating agents, gelling agents, flavorings, emollients, humectants, plasticizers, sweeteners, stabilizing agents, lubricants, bulking agents, preservatives, emulsifiers, acidifying agents, reducing agents, surfactants, carbonating agents, plasticizers, and coatings. A non-limiting catalog of exemplar excipients include acacia, alginate, aluminum acetate, butyl paraben, citric acid, candelilla wax, croscarmellose sodium, confectionary sugar, colloidal silicon dioxide, cellulose, carnuba wax, corn starch, calcium stearate, copolyvidone, hydrogenated castor oil, dimethicone, ethyl cellulose, gelatin, glycerin, glycine, ferric oxide, ferrous oxide, mannitol, magnesium carbonate, methyl paraben, polysorbate 80, polyethylene oxide, propylene paraben, phosphoric acid, polyvinylpyrrolidone, sodium lauryl sulfate, silicon dioxide, stearic acid, sodium metabisulfite, succinic acid, titanium dioxide, triacetin, and triethyl citrate.

Oxidizing agents are chemical compounds that strip electrons from a substrate, often resulting in formation of bonds with one or more oxygen atoms. Common oxidizing agents include hydrogen peroxide, salts of perboric or percarbonic acids, m-chloro-perbenzoic acid, benzoyl peroxide, and sodium hypochlorite.

Embodiments of the invention add water and a predetermined quantity of oxidizing agent to the prescription medicine and wait a predetermined time for a chemical reaction to irreversibly render the active pharmaceutical ingredient biologically inert and safe to discard. The oxidizer may be in the form of a tablet, capsule, gel-cap, powder, gel, or liquid, and the composition may be augmented by one or more excipients to aid in the release of the active pharmaceutical ingredient into aqueous solution.

Use of at least one molar equivalent of oxidizing agent means at least one molar equivalent of oxidizing agent relative to the amount of active pharmaceutical ingredient in the pharmaceutical dosage form. The active pharmaceutical ingredient preferably contains one or more nitrogen atoms, at least one of which is oxidizable by the oxidizing agent.

Figure 2:
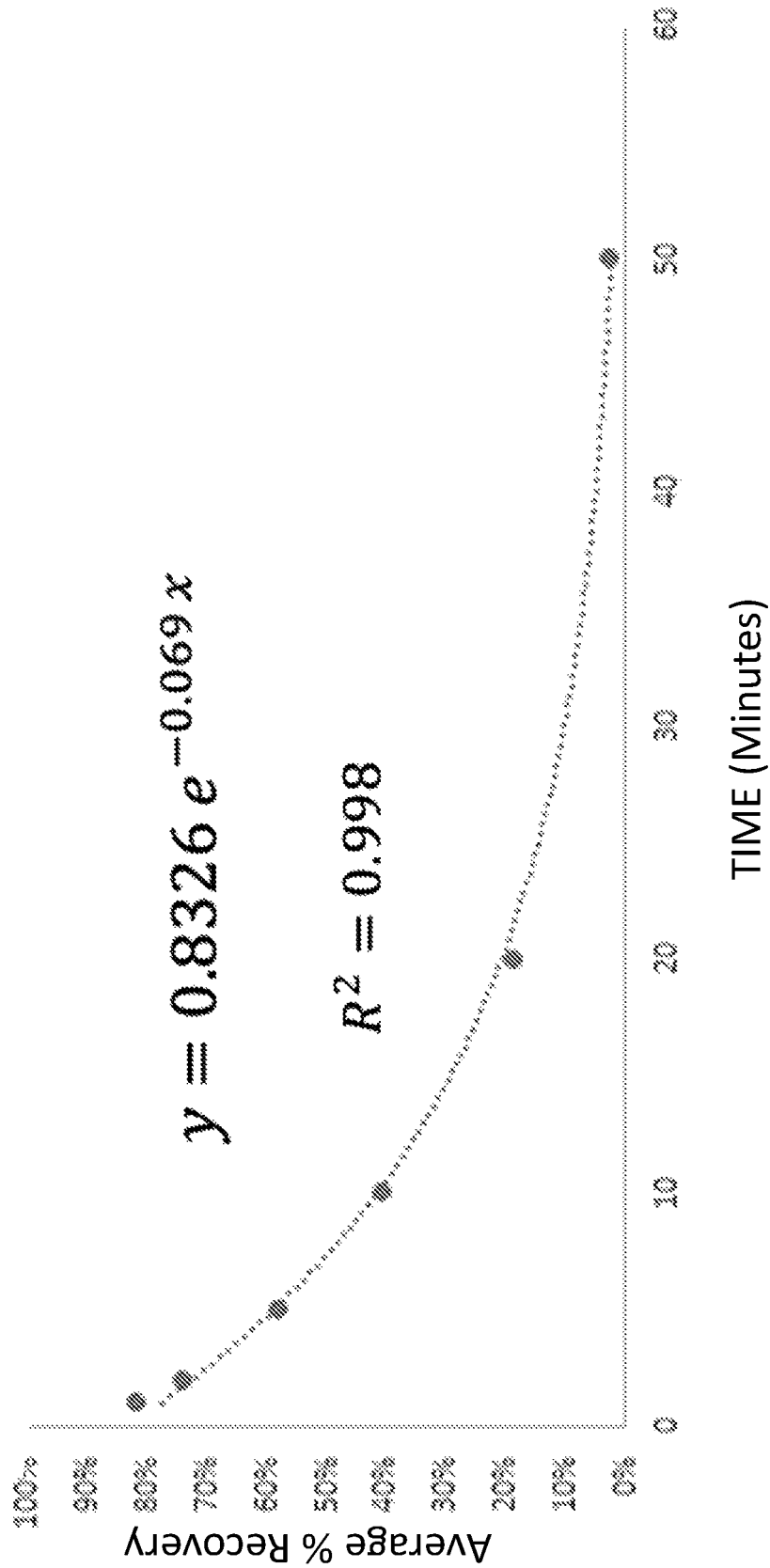
FIG. 2 shows the concentration of oxycodone recovered from an aqueous mixture of saturated sodium perborate as a function of time.

A first embodiment of the invention exploits the kinetics of the reaction between sodium perborate and oxycodone to produce the biologically inactive oxycodone-N-oxide. FIG. 1 shows the chemical structure of oxycodone, representative of opioids as an aromatic, heterocyclic tertiary amine. FIG. 2 plots the concentration of oxycodone hydrochloride in a room temperature aqueous solution of excess sodium perborate. Destruction occurs with an e-folding time of about 20 minutes at room temperature.

Figure 3:
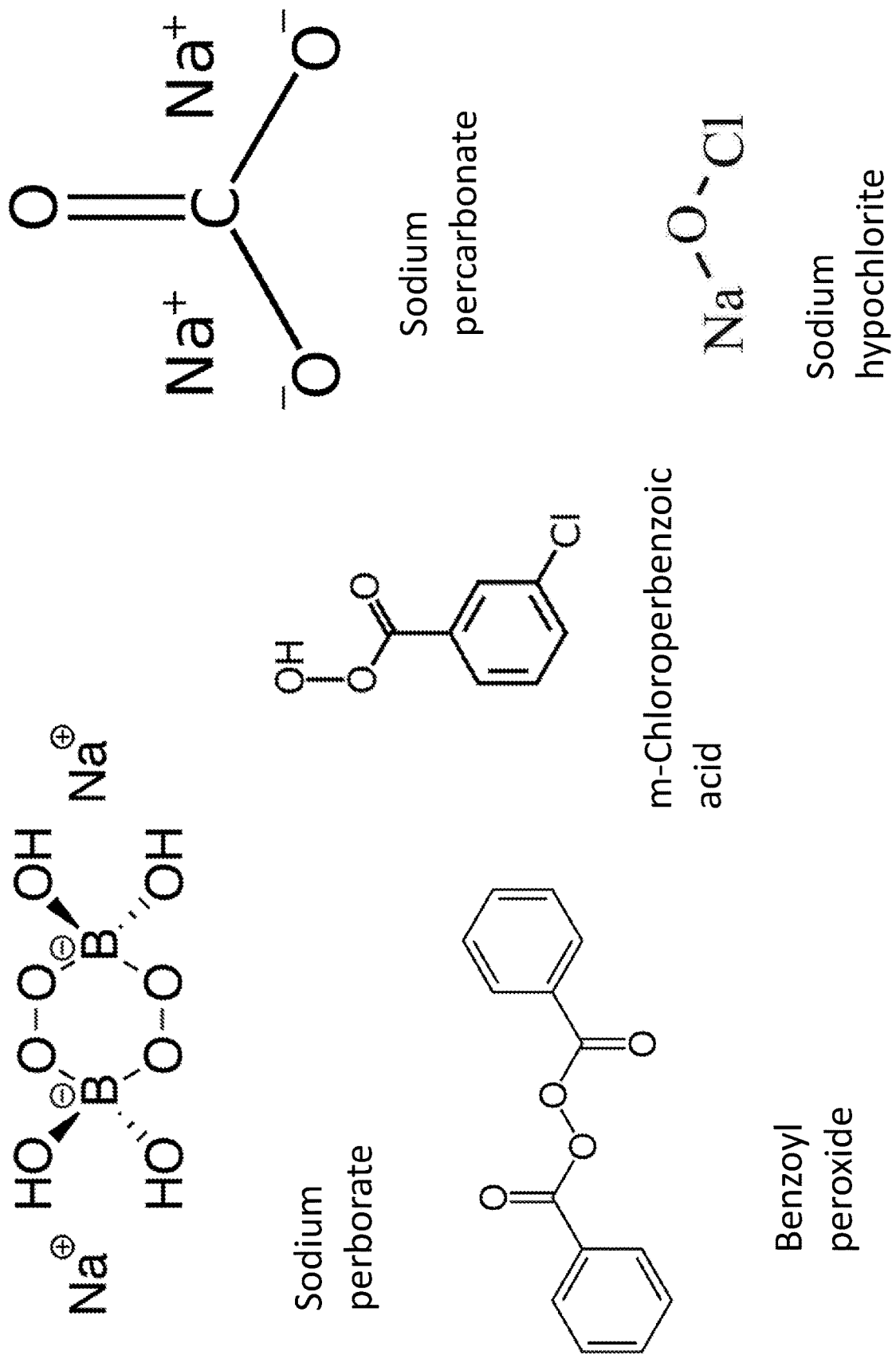
FIG. 3 illustrates the chemical structures of some common oxidizing agents.

Some common alternatives to sodium perborate as the oxidizer are shown in FIG. 3, including sodium percarbonate, m-chloroperbenzoic acid, sodium hypochlorite, and benzoyl peroxide. The m-CPBA is organic and minimally soluble in water, but it completely oxidizes oxycodone in a mixture of alcohol and water within 10 minutes.

Figure 4:
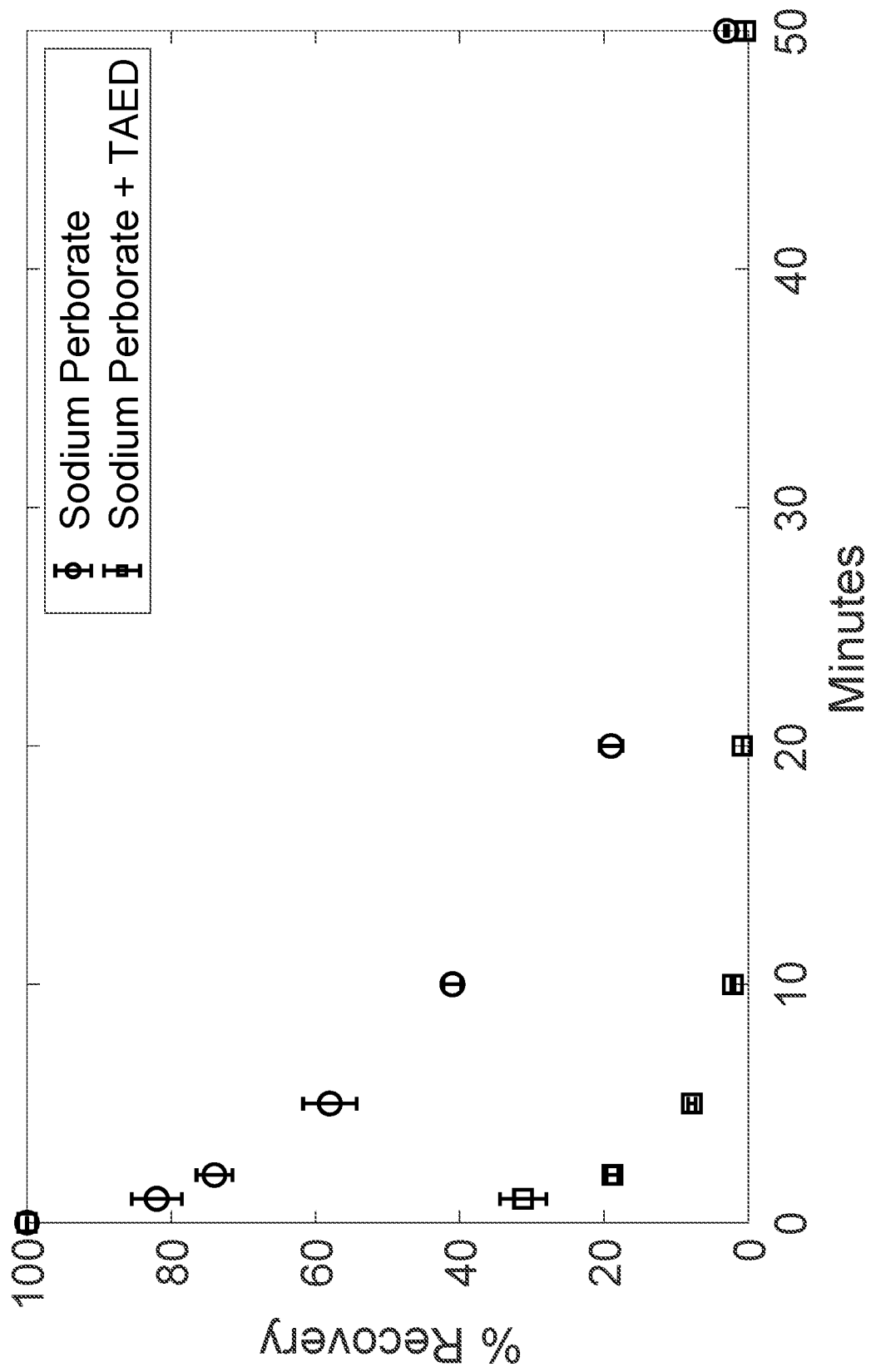
FIG. 4 compares the concentrations of oxycodone as it reacts with two representative oxidizers; sodium perborate in water and sodium perborate with tetraacetylethylenediamine in water.
Figure 5:
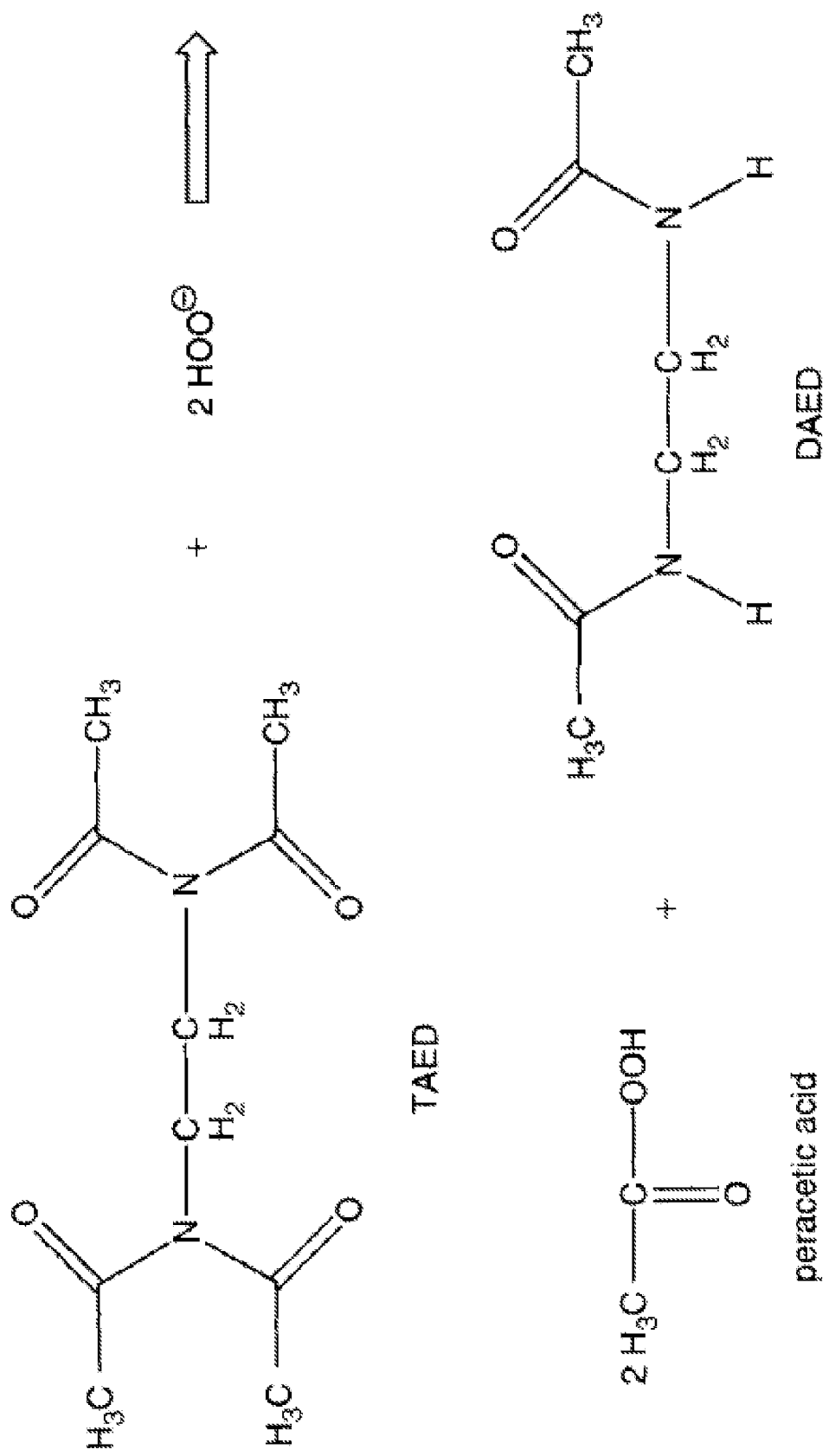
FIG. 5 outlines the chemical mechanism by which peroxide anion that is produced by dissolution of the oxidizers of FIG. 4 interacts with TAED to produce peracetic acid and dieacetyl ethylene diamine (DAED).

A preferred method of employing oxidizing agents provides a bleaching agent that is more reactive with a substrate, thereby accelerating the oxidation reaction. A common example of an intermediate oxidizer is the compound tetra-acetyl ethylene diamine (TAED). Perborate or percarbonate salts produce peroxide anions ($HOO^-$) when dissolved in water. Referring to FIG. 5, TAED reacts with the peroxide anion to generate peracetic acid, a more reactive room temperature oxidizer, and biodegradable diacetyl ethylene diamine (DAED) The consequence of this chemistry is seen in FIG. 4, where the disappearance of oxycodone is ten times faster when TAED is added to sodium perborate.

The time required to render the pharmaceutical safe may vary with the nature of the API and the composition of the oxidizer. FIG. 4 displays the destruction of oxycodone hydrochloride by sodium perborate alone, sodium perborate with TAED Similar experiments using m-CPBA in a water-alcohol mixture (alcohol is added to enhance dissolution of the organic m-CPBA) show complete destruction of oxycodone within ten minutes. The decay rates for these reactions differ by an order of magnitude.

Figure 6:
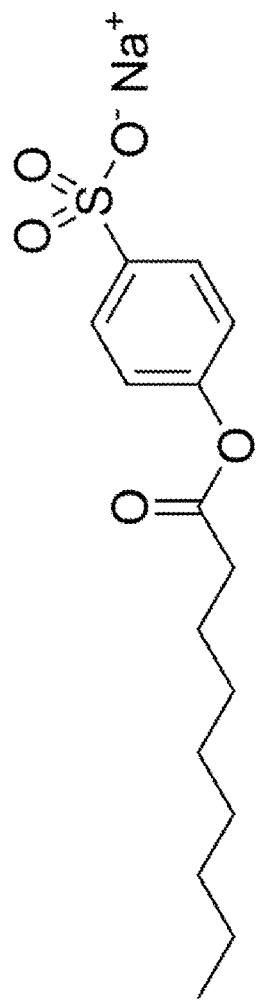
FIG. 6 shows the chemical structures of common accelerants nonanoyloxybenzene sulphonate (NOBS), TAED, and (triethylamoniomethyl)benzoyl caprolactam chloride.
Figure 6:
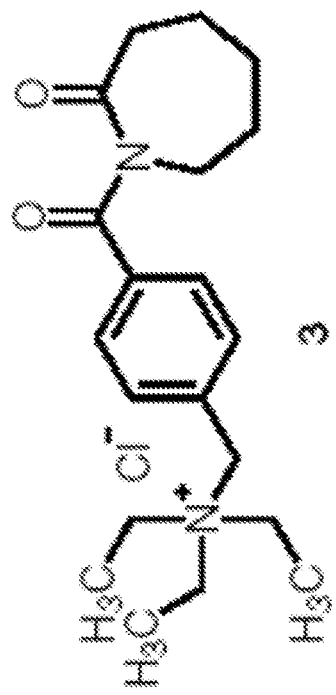
Figure 6:
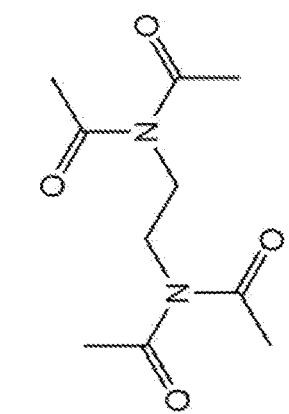

Referring to FIG. 6, bleaching agents or accelerators such as nonanoyloxybenzene sulphonate (NOBS) or (triethylammoniomethyl)benzoyl caprolactam chloride may be substituted for TAED based on the same considerations where oxidizing conditions in room temperature aqueous solutions are desired.

The aim of the invention is to chemically transform the active pharmaceutical ingredient to a biologically or pharmacologically inactive product that is safe to discard in wastewater or solid waste disposal facilities. A biologically or pharmacologically inactive product is a compound that possesses substantially none of the pharmacological activity giving rise to the therapeutic effectiveness of the active pharmaceutical ingredient. Reducing a pharmacological activity of the active pharmaceutical ingredient means that the active pharmaceutical ingredient is transformed to a biologically or pharmacologically inactive product in an amount sufficient to render any unreacted active pharmaceutical ingredient therapeutically ineffective. Preferably, substantially all of the active pharmaceutical ingredient is transformed to a biologically or pharmacologically inactive product. Transforming substantially all of the active pharmaceutical ingredient to a biologically or pharmacologically inactive product renders the active pharmaceutical ingredient safe.

Figure 7A:
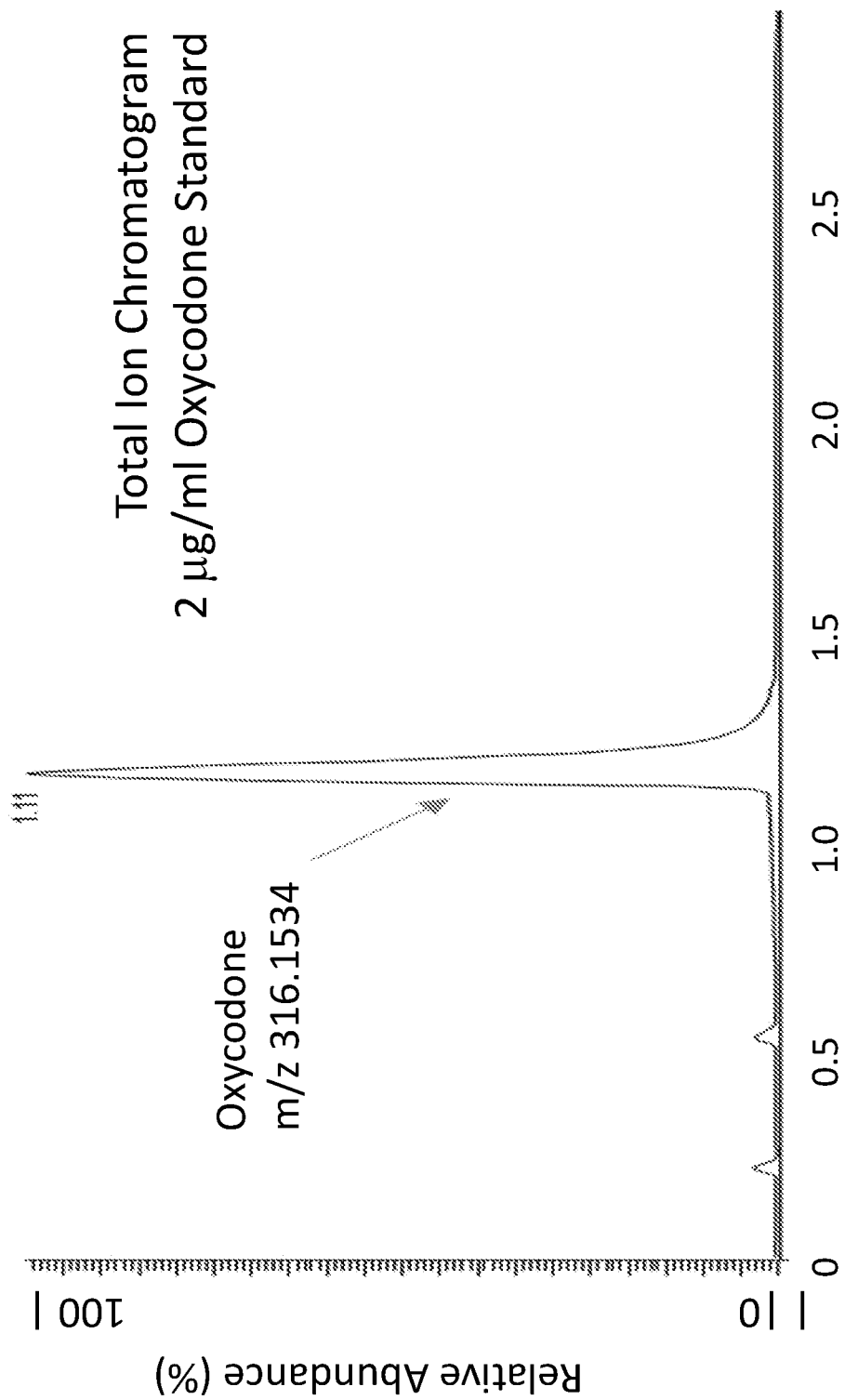
FIG. 7A shows the total ion chromatogram of oxycodone standard.
Figure 7B:
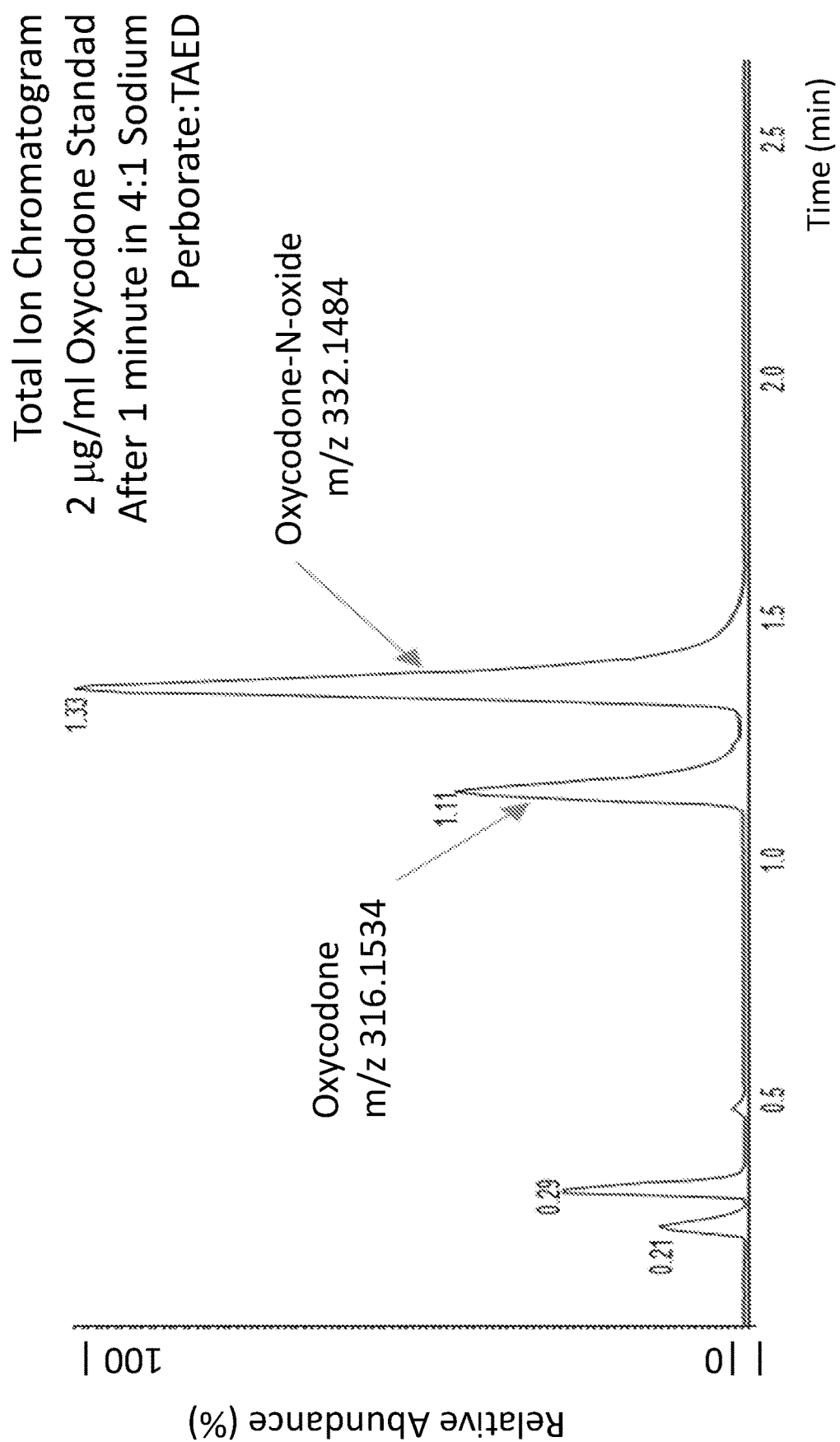
FIG. 7B shows the total ion chromatogram after treatment of oxycodone with 4:1 sodium perborate:TAED for one minute.
Figure 7C:
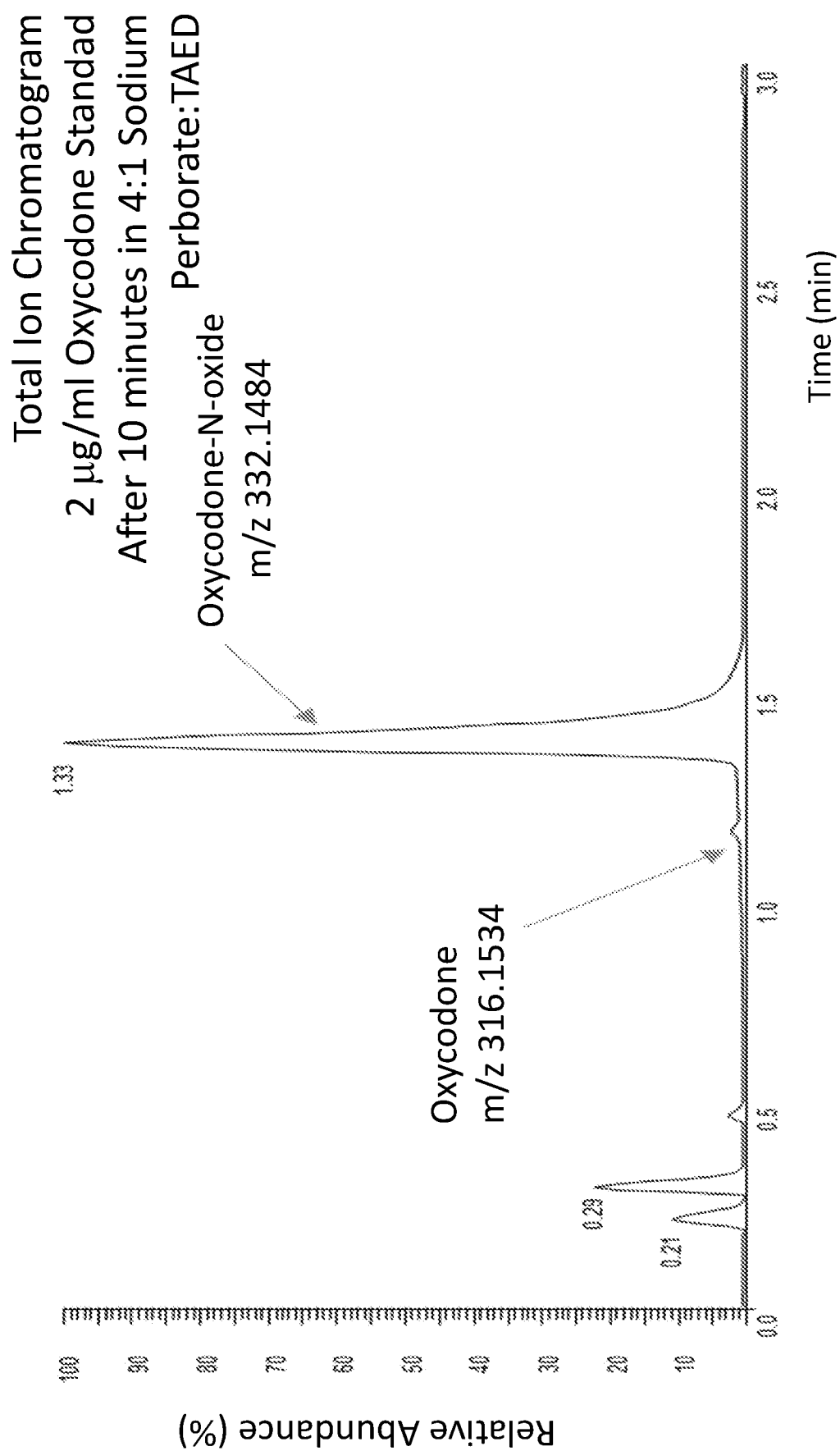
FIG. 7C shows the total ion chromatogram after treatment of oxycodone with 4:1 sodium perborate:TAED for ten minutes.

In the example outlined in FIG. 4 the only measured product is the oxycodone-N-oxide, (molecular weight 332.1484), as can be seen by inspection of the total ion chromatograms at 0, 1, and 10 minutes in FIGS. 7A-C. The identity of this material was confirmed by direct comparison with a pure standard in FIG. 8. The N-oxide form of oxycodone is a standard human metabolite of oxycodone and is excreted safely into the environment by every human that ingests oxycodone.

Figure 9:
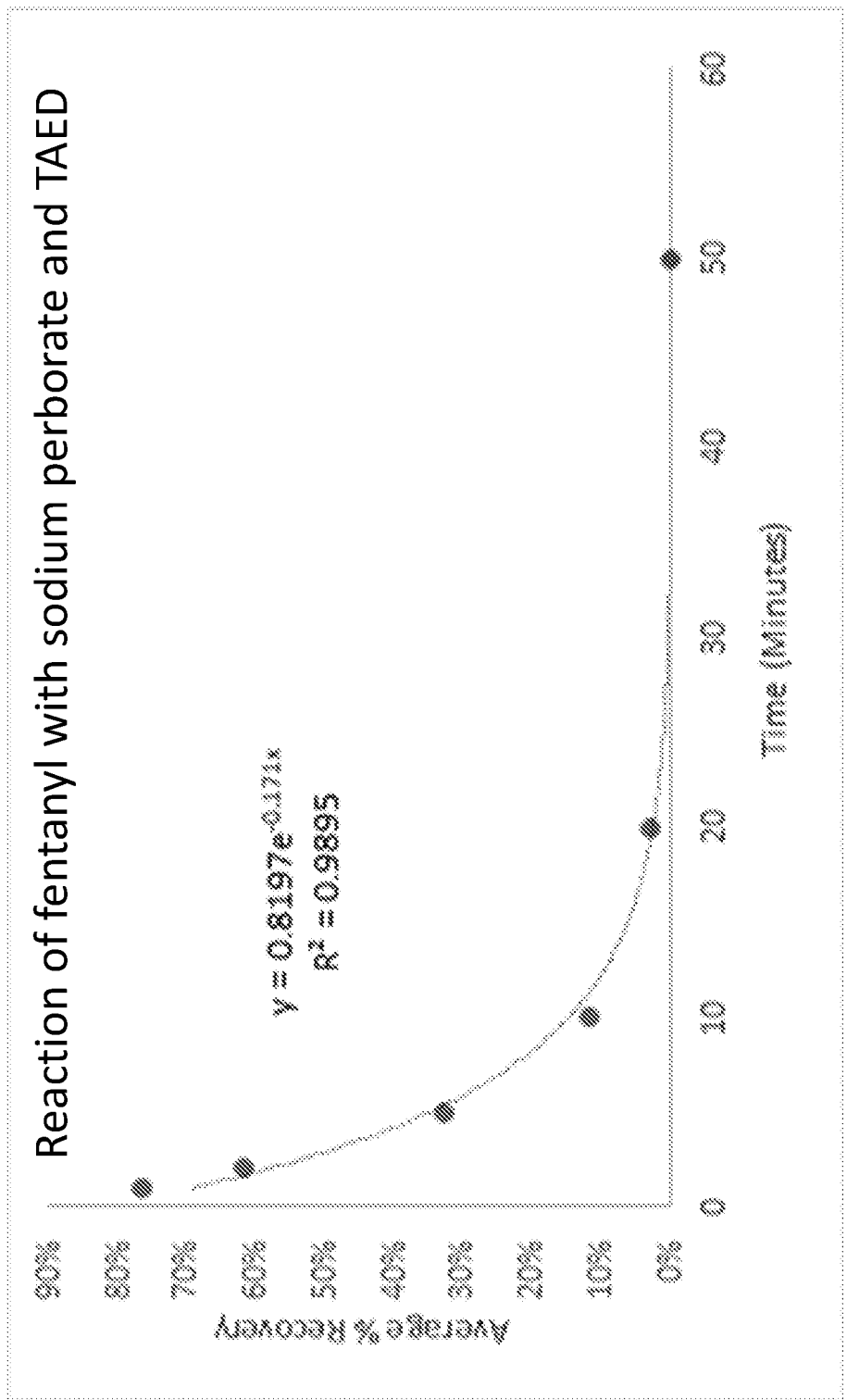
FIG. 9 plots the concentration of fentanyl following addition of a 1:4 mixture of sodium perborate and tetraacetylethylenediamine.
Figure 10A:
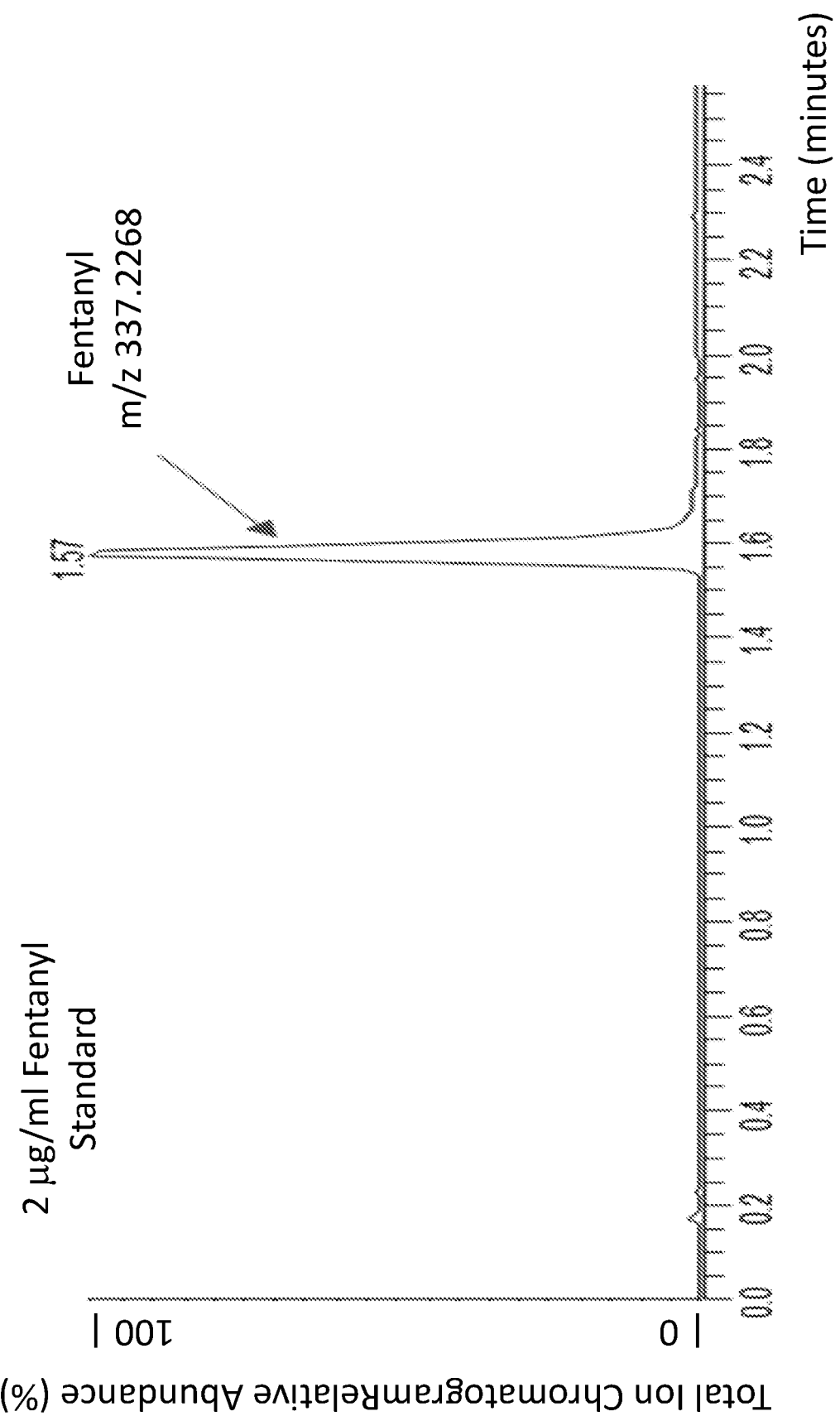
FIG. 10A shows the total ion chromatogram of fentanyl standard.
Figure 10B:
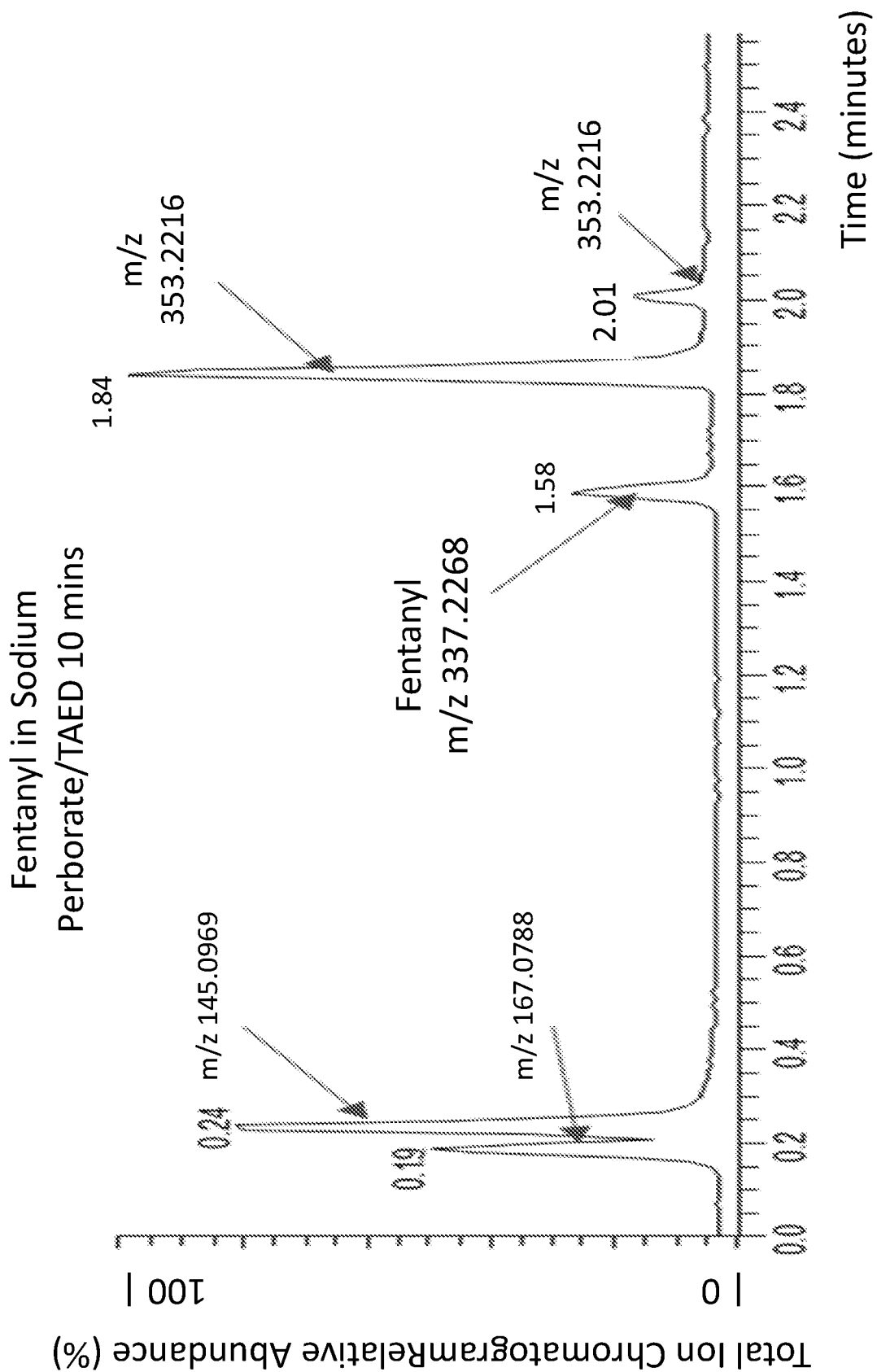
FIG. 10B shows the total ion chromatogram after treatment of fentanyl with sodium perborate/TAED for ten minutes.
Figure 10C:
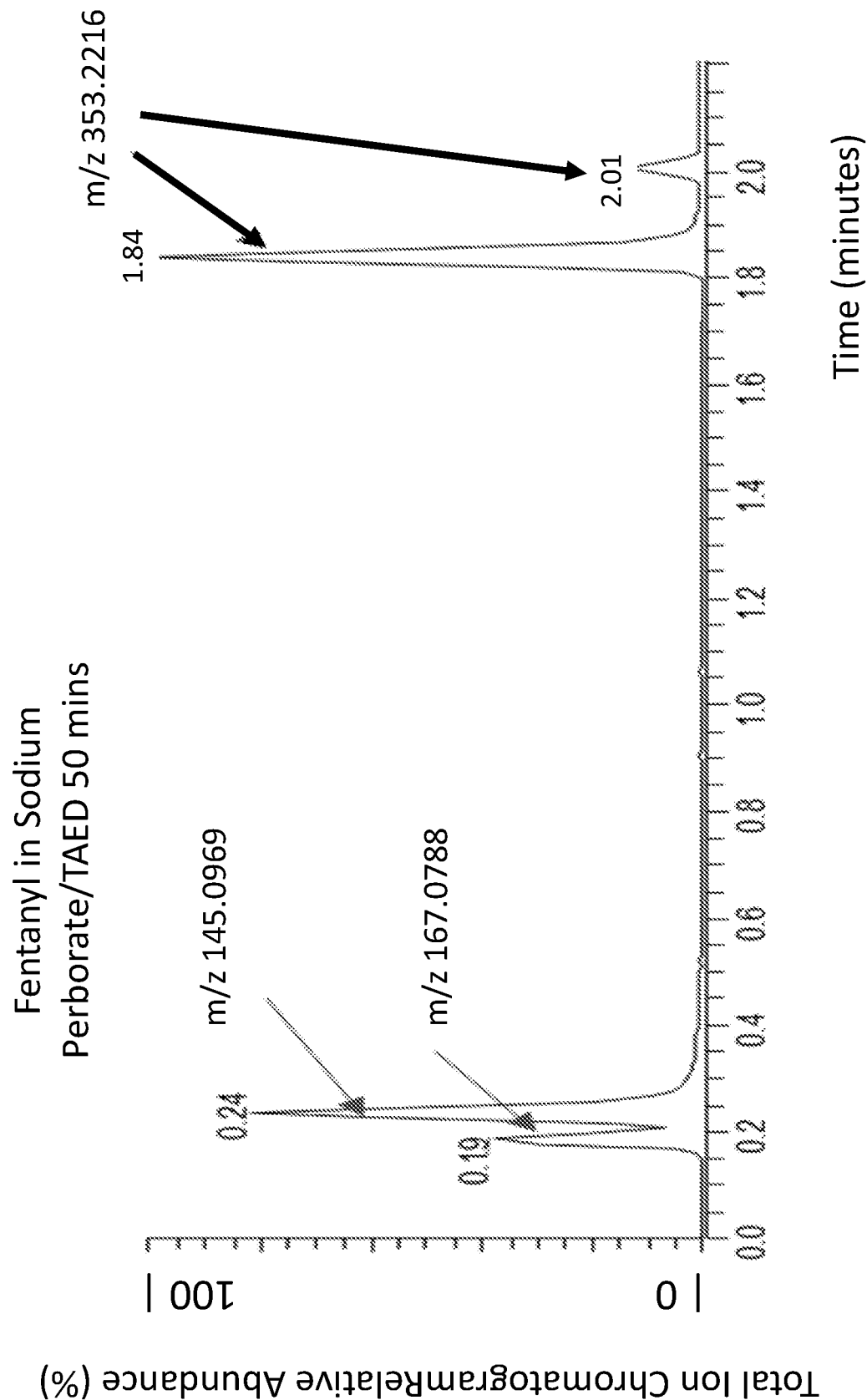
FIG. 10C shows the total ion chromatogram after treatment of fentanyl with sodium perborate/TAED for ten minutes.

The oxidation and dealkylation of the amine nitrogen is a general feature of this class of materials. Fentanyl (FIG. 9) treatment with a 4:1 molar ratio of sodium perborate and TAED is rapidly consumed. Fentanyl-N-oxide is produced as two diastereomers shown in FIG. 1 that are indicated in FIG. 10B-C by mass spectral peaks at 353.2216 and chromatographic retention times of 1.84 and 2.01 minutes.

Figure 11:
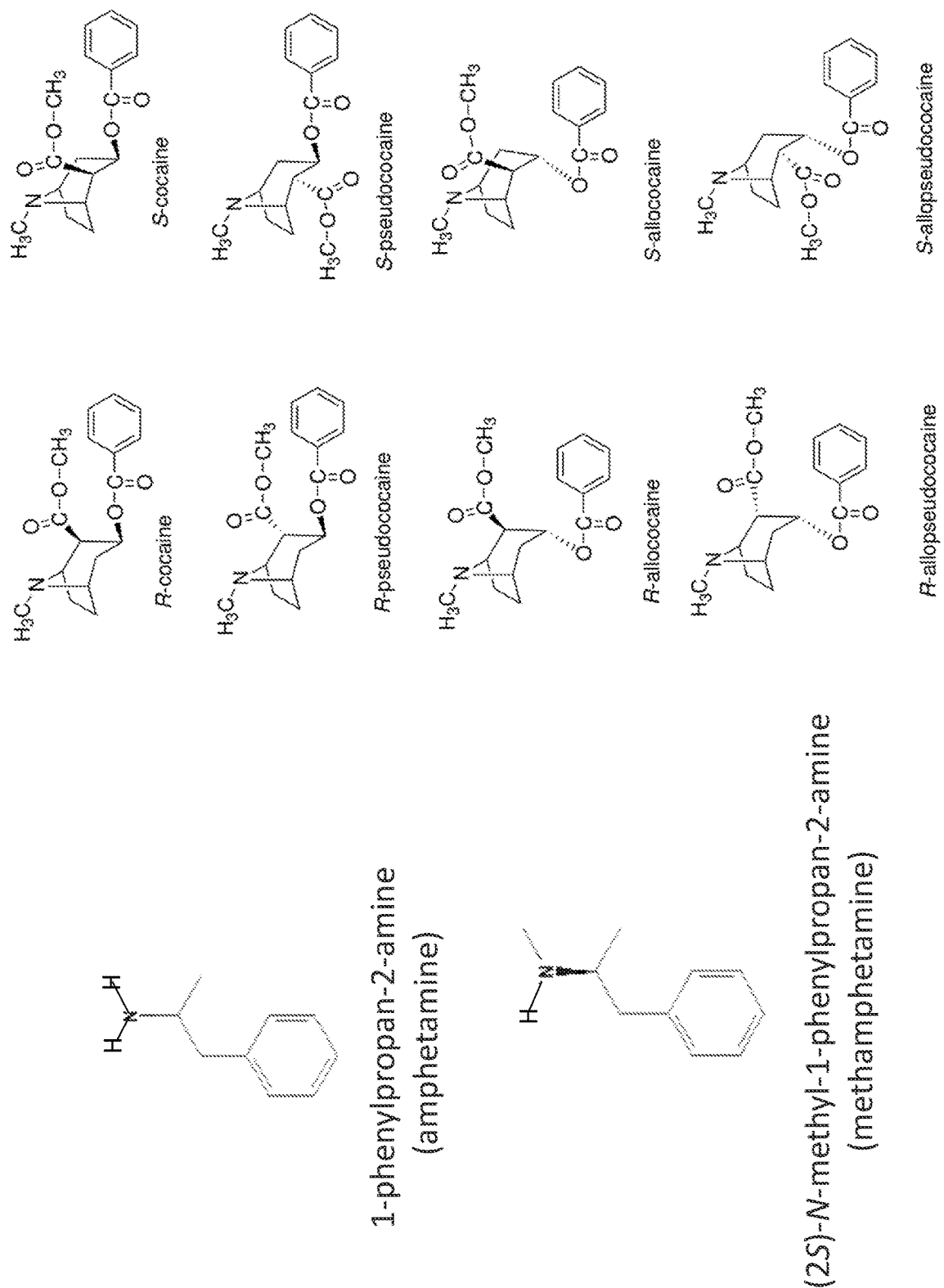
FIG. 11 illustrates stimulants with amine functionalities, including amphetamine and cocaine variants, that are amenable to being rendered safe by oxidation.
Figure 12:
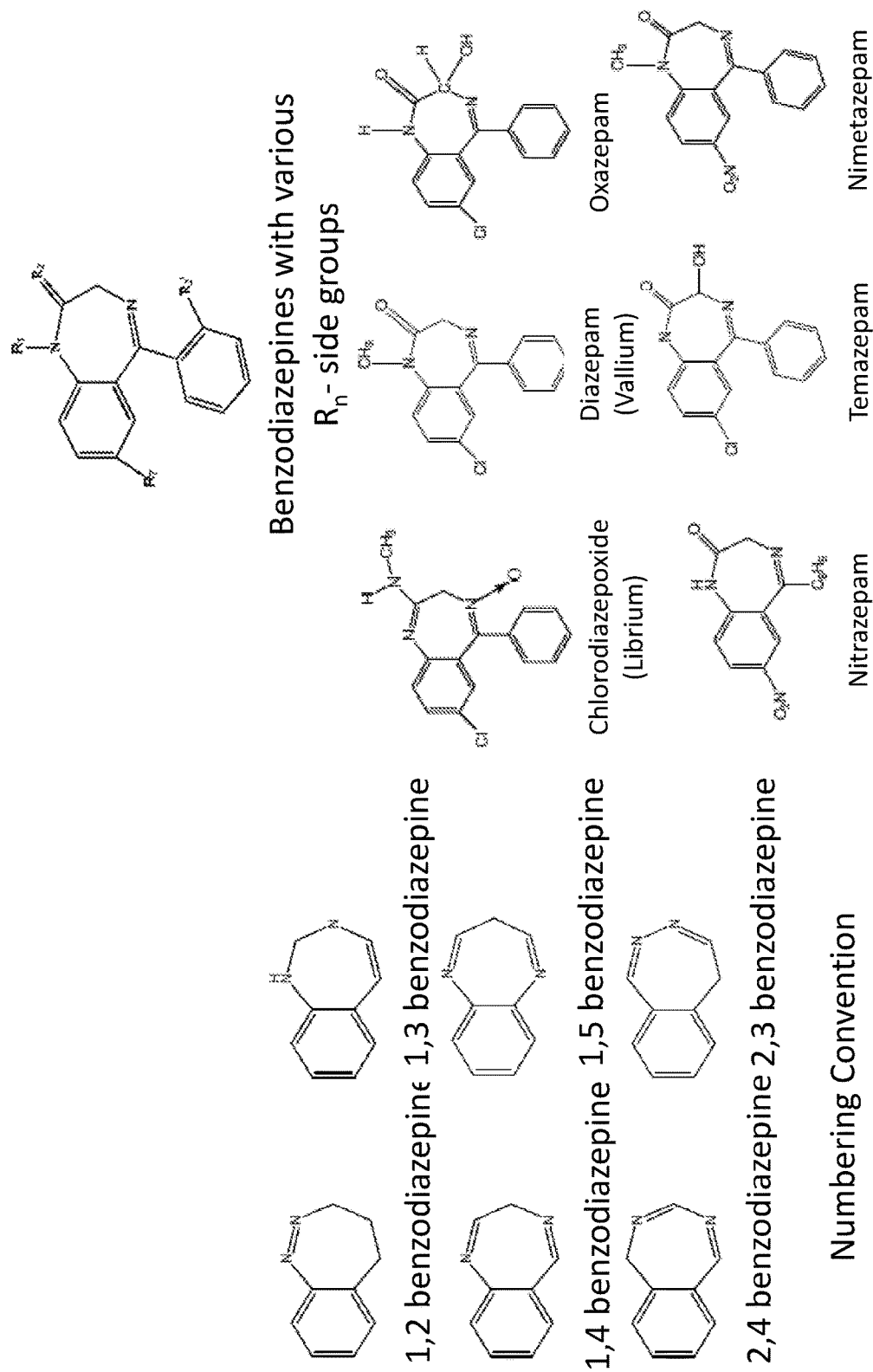
FIG. 12 shows the general structure of antidepressants based on benzodiazepine, the numbering convention for labeling benzodiazepines, and six examples of benzodiazepine pharmaceuticals.

Rendering APIs safe by oxidation or dealkylation of the amine functional group is also suited to stimulants such as amphetamine, cocaine, and their variants, some of which are displayed in FIG. 11. The same approach is effective for the benzodiazepines, whose general form and a few common examples are illustrated in FIG. 12. All of these compounds have amine groups that are essential to their biological activity; oxidation of the amine generally eliminates their biological efficacy and renders them safe for disposal.

Figure 13:
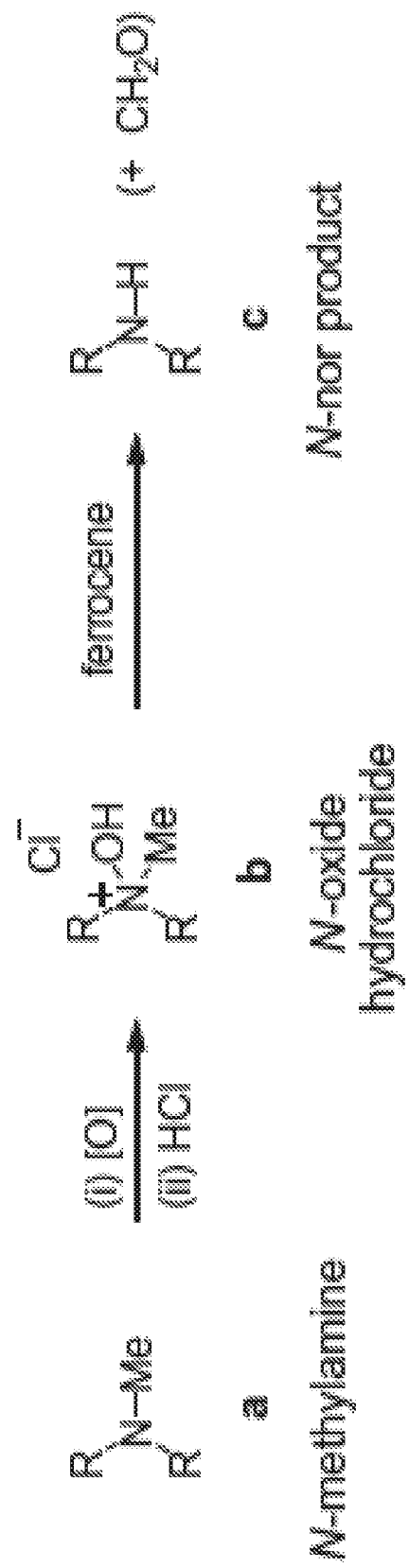
FIG. 13 illustrates an optional additional reactive transformation of an amine-based pharmaceutical where ferrocene catalyzed dealkylation follows generation of the N-oxide.

Another embodiment of the invention adds catalytic materials for further reaction of the N-oxides. For example, the N-oxides of alkaloids have been demethylated by a sub-stoichiometric reaction with ferrocene $((C_5H_5)_2Fe)$, as described by Kok and Scammells, *Bioorganic and Medicinal Chemistry Letters,* 20, 4499 (2010) and shown schematically in FIG. 13.

An advantage of the proposed method is that the active ingredients are generally recognized as safe because they are widely used in commercial detergents, so they are convenient to handle and safe to discard in wastewater or landfills.

Another advantage of the invention is that the reactions can be accomplished at room temperature using tap water.

Yet another advantage of the method is that the oxidation products are those that are naturally generated when opioids are consumed and degraded by human biology.

Still another advantage of the method is that the commodity materials from which the oxidizer compositions are formulated are much less costly on a per-pill-destroyed basis than competitive approaches that rely on physisorption.

Embodiments of the method provide the oxidizer, and optionally the accelerant, in varied physical forms including tablets, powders, gel-caps, capsules, or gels based on cost, convenience, and environmental impact. In a preferred embodiment the oxidizers are embedded in a water soluble matrix that is incorporated into the cap or base of the pharmaceutical dosage form container (e.g., opioid vial) so that a consumer can just add water to the prescription vial, shake, and wait a prescribed period while the active material renders the API safe. A water soluble matrix is a solid material in which the active ingredient (here oxidizer(s)) are embedded and subsequently released on contact with liquid water. These materials include both synthetic, semi-synthetic, and natural polymers such as polyethylene glycol, polyvinyl alcohol, soluble carbohydrates (e.g. glucose), polyvinyl pyrrolidone, polyacrylic acid, and others as described, for example, in. Kadajji and Betageri, Water Soluble Polymers for Pharmaceutical Applications Polymers 2011, 3, 1972-2009; doi:10.3390/polym3041972.

Some pharmaceutical formulations contain coatings and binders that affect their solubility properties. For example, oxycontin contains ammonio-methacrylate copolymer that coats the API and slowly dissolves to control the dose of oxycodone released over time. As will be apparent, the present method may be enhanced by addition of chemicals that accelerate the release of API into solution. In the case of the methacrylate copolymers the addition of liquid ethanol or methanol or solid cyclohexanol would serve this purpose. Another example of solubility enhancement arises from sugar coated tablets. Sugar-based coatings mitigate tablet bitterness, but may have reduced rates of dissolution at normal pH; addition of acidifiers such as citric acid to the formulation accelerates dissolution of the coating and release of the API into aqueous solution. The term "solubility enhancer" as used herein is a composition that accelerates dissolution of excipients and coatings and thereby aiding in the rendering of the active pharmaceutical ingredient into aqueous solution. (examples include detergents, pH buffers, surfactants, and the like).

Another embodiment of the invention renders bulk quantities of opioids safe. As will be obvious to those with chemistry experience, a mixture of oxidizer and optional accelerant can be combined in a blender with water and excess opioids, stirred for an appropriate time at room or elevated temperature, and disposed of in wastewater after conversion to the N-oxides are complete. The oxidizer mixture may be provided as pre-weighed tablets, pouches, water-soluble packets, or the like to ensure that the reactants are in molar excess of the API to be rendered safe. This approach may be useful to law enforcement agencies, hospitals, pharmacies, and other collection points where excess opioids are logistically problematic.

Examples

A first example renders safe a 40 ml prescription bottle containing 20 tablets of oxycodone hydrochloride (20 mg/tablet dose). A tablet comprised of at least 176 mg of sodium perborate and about 300 mg of excipients that facilitate tableting, storage, and dissolution is added. The vial is filled with tap water, capped, and allowed to stand for one hour to complete transformation of the API to the N-oxide form. The vial may optionally be shaken, and the tap water may be heated, actions that accelerate the conversion to the N-oxide. The liquid residue is safe to discard in wastewater, or as solid waste after the liquid phase is evaporated because the N-oxide is precisely the form that is produced by human livers before it is excreted in urine.

Figure 8:
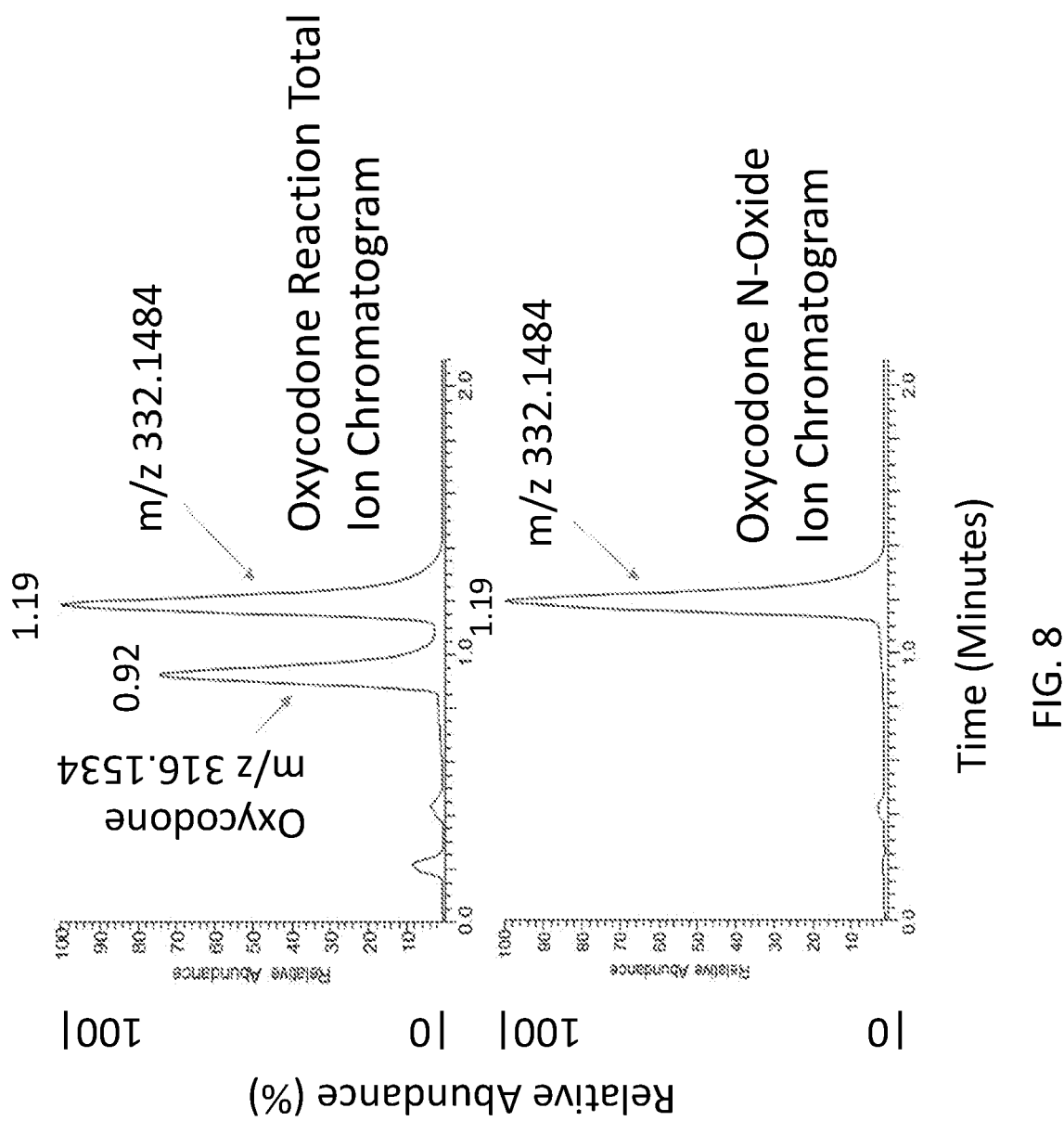
FIG. 8 displays chromatograms that confirm the product peak from FIGS. 7B and C is oxycodone-N-oxide by comparison with a pure standard.

A second example of the invention employs a capsule comprised of TAED and sodium percarbonate in a 1:4 molar ratio. A vial with 10, 10 mg dose tablets of oxycodone is treated with water and a gelatin capsule containing not less than 16 mg of TAED and not less than 45 mg of sodium perborate. Rendering the oxycodone safe happens swiftly at room temperature with the combined formulation, as can be seen in the total ion chromatograms of FIG. 4, where the e-folding time is about one minute and the conversion to the N-oxide is complete after ten minutes. FIG. 8 shows reference chromatograms that confirm the identity of the ion peak at 1.33 minutes retention time and m/z=332.1484 as oxycodone-N-oxide.

Figure 14B:
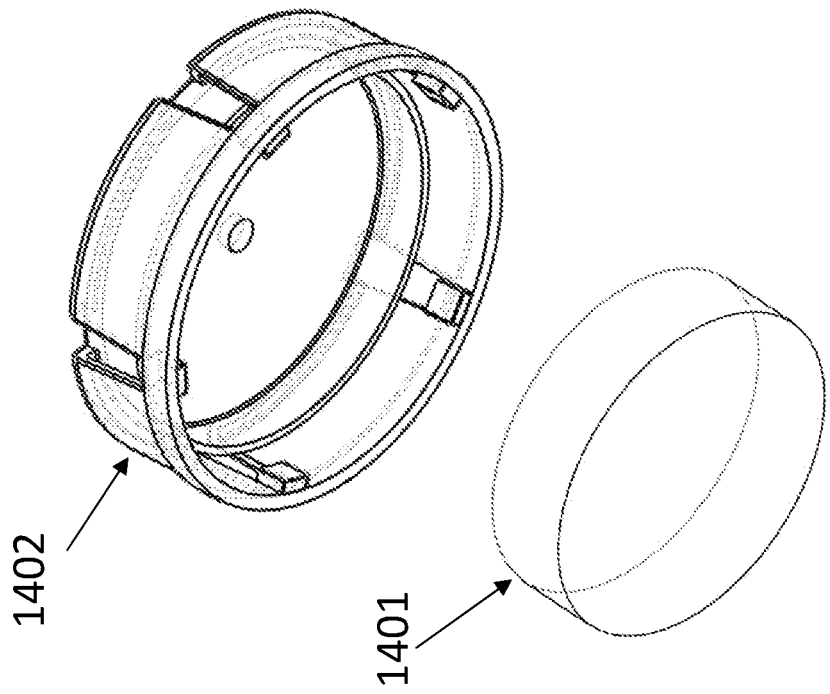
FIG. 14B shows an oxidizing tablet wrapped in a water-soluble coating and bottom view of a vial cap.
Figure 14A:
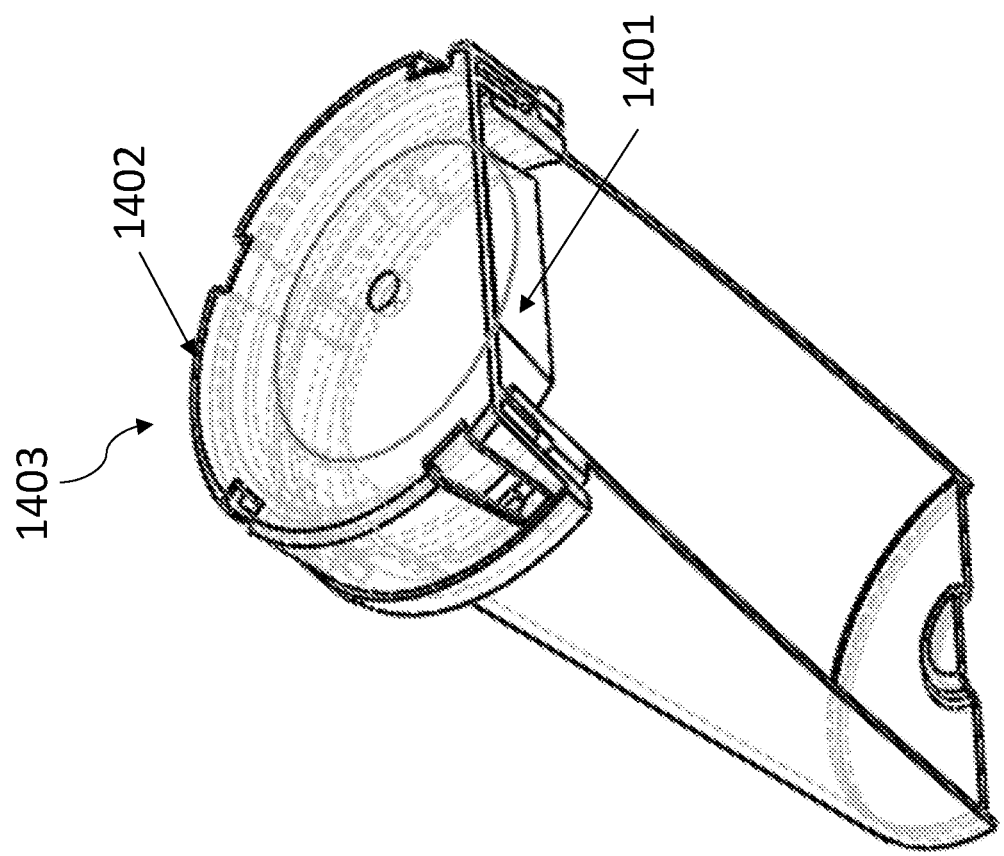
FIG. 14A shows one embodiment of the invention comprising an oxidizing tablet wrapped in a water-soluble coating and incorporated into one side of a vial cap.

A third example of the invention employs a vial cap that may be reversible and has a water-soluble pouch containing oxidizer, accelerant, and ferrocene catalyst sealed with polyvinyl alcohol. The pouch or tablet (1401) is incorporated into the exterior body of the cap as outlined in FIG. 14A-B. It may alternatively be incorporated into the normally exterior face of the cap and reversed for mixing of the composition with water and the active pharmaceutical ingredients using the bottle (1403) as a reaction vessel. The residual pharmaceuticals are rendered safe by filling the prescription vial with water, inverting the cap to expose the polyvinyl alcohol pouch to the solution of API, shaking to release the oxidizing formulation into solution, and waiting a prescribed time for the oxidation to be complete. This approach may optionally be used by embedding the water-soluble matrix into the interior surface of the cap or at the bottom of the pill bottle itself. While this may be more convenient for the consumer, it has the disadvantage that interaction of the API with the oxidizer before disposal is desired must be avoided by ensuring mechanical isolation is complete as long as the interior remains dry.

A fourth example of the invention renders a 34 gram quantity of seized fentanyl-containing narcotics safe. Optionally, a small sample could be retained for evidentiary purposes or detailed chemical analysis. Conservatively presuming that the material is pure fentanyl citrate (molecular weight 336.5 g/mole) this would require a minimum of 11.4 grams (0.05 mole) of TAED and 62 grams (0.2 mole) of sodium perborate tetrahydrate to completely oxidize the active pharmaceutical ingredient. At neutral pH the solubility of fentanyl is only 2 grams per liter, however this is substantially enhanced to 65 g/l at pH=5.7, so the composition preferably includes a buffer to adjust the pH; a mixture of citric acid monohydrate and sodium hydrogen phosphate may be used. A kit for destroying 34 g of fentanyl would therefore be a heat-sealed polyvinyl alcohol pouch with 11.4 grams of TAED, 62 grams of sodium perborate tetrahydrate, 18.9 grams of citric acid monohydrate, and 3.6 grams of sodium hydrogen phosphate. The process would add the seized material to a blender with one liter of tap water and the water-soluble pouch. The mixture would be blended for five minutes at low speed to ensure complete mixing and reaction of the active pharmaceutical composition. It would then be safe to flush down the toilet or drain.

A fifth example of the invention is a kit comprised of an empty plastic vial into which a mixture of sodium percarbonate, TAED, and citric acid are pre-measured to accommodate the destruction of a predetermined number and type of prescription medicine. The citric acid is included to safely mimic the acidic conditions of the stomach to enhance release of the API from the medication's excipients, and the size of the vial is selected to ensure adequate dissolution of both the oxidizers and API for the predetermined number of tablets.

A sixth example of the invention dispenses the oxidizer as tablets, gel-caps, or pouches whose composition is tailored to render a fixed quantity and type of medicine safe. Tablets containing 88 mg of sodium perborate tetrahydrate, 32 mg of TAED, and 180 mg of inert excipients would suffice to destroy up to 10, 20 mg doses of oxycodone hydrochloride. These tablets could be dispensed in bubble packs so that a consumer could adjust the number of oxidizer tablets based on the number and dose of medication on that they wish to render safe.

It is to be understood that both the foregoing general description and the following detailed description are exemplary and explanatory only and are not restrictive of the disclosed subject matter, as will be set forth in the claims.

For reasons of completeness, various aspects of the invention are set out in the following numbered clauses, which are not intended to be exhaustive:

Clause 1. A method for rendering unused pharmaceuticals safe by reacting them with at least one molar equivalent of oxidizing agent in water;
  (a) where the pharmaceutical agent has one or more nitrogen atoms that, when oxidized, reduce the activity of the agent; and
  (b) where the pharmaceutical agent is an opioid, an amphetamine, a cocaine variant, or a benzodiazepine derivative.

Clause 2. A method for rendering unused pharmaceuticals safe by reacting them with at least one molar equivalent of oxidizing agent and an organic peroxide accelerant, where the accelerant is one or more of tetra-acetylethylenediamine, nonanolyloxybenzene sulphonate, and triethylammonium benzoyl caprolactam chloride.

Clause 3. The method of claim 1 or claim 2 where the oxidizing agent is in the form of a tablet, gel-cap, capsule, gel, or powder.

Clause 4. The method of claim 1 or claim 2 wherein the oxidizing agent is embedded in a water soluble matrix inside the cap or vial containing unused pharmaceuticals, wherein the oxidizing agent is encased in polyvinyl alcohol.

Clause 5. The method of claim 1 or 2 wherein the opioid is a semi-synthetic opioid selected from the list {hydromorphone, hydrocodone, oxycodone, oxymorphone, ethylmorphine, and buprenorphine}.

Clause 6. The method of claim 1 or 5 wherein the opioid is a fully synthetic opioid selected from the list {fentanyl, pethidine, levorphanol, methadone, tramadol, tapentadol, and dextropropoxyphene.}

Clause 7. The method of claim 1 or 5 wherein the water is heated to a temperature above about 60° C. to accelerate the chemical transformation.

Clause 8. The method of claim 1 or claim 5 wherein the release of the pharmaceutical into aqueous solution is enhanced by addition of an acid, base, or alcohol.

Clause 9. The method of claim 1 or 5 wherein the mixture is heated to a temperature above about 60° C. and below about 100° C. in a microwave oven to accelerate the chemical transformation.

Clause 10. A kit for rendering pharmaceuticals suitable for disposal comprising a percarbonate or perborate salt, TAED, and excipients compressed into a water soluble tablet.

Clause 11. A kit for rendering pharmaceuticals suitable for disposal comprising a percarbonate or perborate salt, NOBS, and excipients compressed into a water soluble tablet.

Clause 12. A kit for rendering pharmaceuticals suitable for disposal comprising a vial and cap with a percarbonate or perborate salt embedded in a water soluble matrix and molded into the vial or its cap.

Clause 13. A system for rendering bulk pharmaceuticals safe comprising a blender, water, and a mixture of oxidizer, optional accelerant, and optional solubility enhancers.

In the following, embodiments of the invention are disclosed. The first embodiment is denoted E1, the second embodiment is denoted E2 and so forth.

E1. A method for disposing of a pharmaceutical dosage form comprising:
contacting the pharmaceutical dosage form with an aqueous mixture comprising at least one molar equivalent of an oxidizing agent, wherein the pharmaceutical dosage form comprises an active pharmaceutical ingredient having one or more nitrogen atoms;
releasing the active pharmaceutical ingredient from the pharmaceutical dosage form; and
reacting the active pharmaceutical ingredient with the oxidizing agent, wherein reacting the active pharmaceutical ingredient reduces a pharmacological activity of the active pharmaceutical ingredient.

E1.1. The method of E1, wherein reacting the active pharmaceutical ingredient with the oxidizing agent reduces the pharmacological activity of the active pharmaceutical ingredient.

E1.2. The method of E1 or E1.1, wherein the oxidizing agent oxidizes at least one of the one or more nitrogen atoms.

E2. The method of any of E1 to E1.2, wherein the aqueous mixture further comprises one or more organic peroxide accelerants.

E3. The method of any of E1 to E2 wherein the reaction of the active pharmaceutical ingredient with the oxidizing agent is heated to a temperature above about 60° C.

E4. The method of any of E1 to E2 wherein the reaction of the active pharmaceutical ingredient with the oxidizing agent is heated to a temperature above about 60° C. and below about 100° C.

E5. The method of E4, wherein the reaction is heated in a microwave oven.

E6. The method of any of E1 to E5, wherein the aqueous mixture further comprises an acid, a base, or an alcohol.

E7. The method of E6, wherein the acid, base, or alcohol enhances release of the active pharmaceutical ingredient from the pharmaceutical dosage form.

E8. The method of any of E1 to E7, wherein the active pharmaceutical ingredient is an opioid, an amphetamine, cocaine, a benzodiazepine, or a derivative thereof.

E8.1. The method of E8, wherein the active pharmaceutical ingredient is the opioid or derivative thereof.

E8.2. The method of E8, wherein the active pharmaceutical ingredient is the amphetamine or derivative thereof.

E8.3. The method of E8, wherein the active pharmaceutical ingredient is cocaine or a derivative thereof.

E8.4. The method of E8, wherein the active pharmaceutical ingredient is the benzodiazepine or derivative thereof.

E9. The method of E8 or E8.1, wherein the active pharmaceutical ingredient is a semisynthetic opioid.

E10. The method of E8 or E8.1, wherein the active pharmaceutical ingredient is a fully synthetic opioid.

E11. The method of E8 or E8.1, wherein the active pharmaceutical ingredient is selected from the group consisting of hydromorphone, hydrocodone, oxycodone, oxymorphone, ethylmorphine, and buprenorphine.

E11.1. The method of E11, wherein the active pharmaceutical ingredient is hydromorphone.

E11.2. The method of E11, wherein the active pharmaceutical ingredient is hydrocodone.

E11.3. The method of E11, wherein the active pharmaceutical ingredient is oxycodone.

E11.4. The method of E11, wherein the active pharmaceutical ingredient is oxymorphone.

E11.5. The method of E11, wherein the active pharmaceutical ingredient is ethylmorphine.

E11.6. The method of E11, wherein the active pharmaceutical ingredient is buprenorphine.

E12. The method of E8 or E8.1, wherein the active pharmaceutical ingredient is selected from the group consisting of fentanyl, pethidine, levorphanol, methadone, tramadol, tapentadol, and dextropropoxyphene.

E12.1. The method of E12, wherein the active pharmaceutical ingredient is fentanyl.

E12.2. The method of E12, wherein the active pharmaceutical ingredient is pethidine.

E12.3. The method of E12, wherein the active pharmaceutical ingredient is levorphanol.

E12.4. The method of E12, wherein the active pharmaceutical ingredient is methadone.

E12.5. The method of E12, wherein the active pharmaceutical ingredient is tramadol.

E12.6. The method of E12, wherein the active pharmaceutical ingredient is tapentadol.

E12.7. The method of E12, wherein the active pharmaceutical ingredient is dextropropoxyphene.

E13. The method of any of E2 to E12.7, wherein the one or more organic peroxide accelerants is selected from the group consisting of tetra-acetylethylenediamine (TAED), nonanolyloxybenzene sulphonate (NOBS), and triethylammonium benzoyl caprolactam chloride.

E13.1. The method of E13, wherein the one or more organic peroxide accelerants is TAED.

E13.2. The method of E13, wherein the one or more organic peroxide accelerants is NOBS.

E13.3. The method of E13, wherein the one or more organic peroxide accelerants is triethylammonium benzoyl caprolactam chloride.

E14. The method of any of E1 to E13.3, further comprising releasing the oxidizing agent from a tablet, gel-cap, capsule, gel, or powder.

E14.1. The method of E14, comprising releasing the oxidizing agent from the tablet.

E14.2. The method of E14, comprising releasing the oxidizing agent from the gel-cap.

E14.3. The method of E14, comprising releasing the oxidizing agent from the capsule.

E14.4. The method of E14, comprising releasing the oxidizing agent from the gel.

E14.5. The method of E14, comprising releasing the oxidizing agent from the powder.

E15. The method of any of E1 to E14.5, further comprising releasing the oxidizing agent from a water soluble matrix.

E16. The method of any of E1 to E14.5, further comprising releasing the oxidizing agent from a polyvinyl alcohol casing.

E17. The method of any of E1 to E16, wherein the pharmaceutical dosage form is a solid dosage form.

E18. The method of any of E1 to E17, further comprising contacting the pharmaceutical dosage form with the aqueous mixture in a pharmaceutical dosage form container.

E19. The method of E18, further comprising releasing the oxidizing agent from a compartment in the pharmaceutical dosage form container.

E20. The method of E19, wherein the compartment is inside the cap of the pharmaceutical dosage form container.

E21. The method of any of E1 to E20, wherein reacting the active pharmaceutical ingredient with the oxidizing agent provides a disposal mixture.

E22. The method of E21, further comprising disposing of the disposal mixture.

E23. The method of any of E1 to E22, wherein the oxidizing agent is a percarbonate salt.

E23.1. The method of any of E1 to E22, wherein the oxidizing agent is a perborate salt.

E24. A tablet comprising an oxidizing agent and one or more excipients.

E25. The tablet of E24, wherein the tablet further comprises one or more organic peroxide accelerants.

E25.1. The tablet of E25, wherein the tablet comprises the one or more organic peroxide accelerants of any of E13 to E13.3.

E26. The tablet of any of E24, E25, or E25.1, wherein the oxidizing agent is a percarbonate salt.

E26.1. The tablet of any of E24, E25, or E25.1, wherein the oxidizing agent is a perborate salt.

E27. The tablet of any of E25 to E26.1, wherein the one or more organic peroxide accelerants is TAED.

E28. The tablet of any of E25 to E26.1, wherein the one or more organic peroxide accelerants is NOBS.

E29. The tablet of any of E24 to E28, wherein the tablet is water soluble.

E30. A kit comprising the tablet of any of E24 to E29 and a packaging, the packaging containing the tablet.

E31. The kit of E30, wherein the packaging is a pouch or a water-soluble packet.

E32. The kit of E31 or E32, further comprising a container and a cap adapted to fit the container.

E33. A kit comprising:
(a) a container;
(b) a cap adapted to fit the container; and
(c) an oxidizing agent embedded in a water-soluble matrix.

E34. The kit of E33, further comprising one or more organic peroxide accelerants embedded in the water-soluble matrix.

E34.1. The kit of E34, wherein the kit comprises the one or more organic peroxide accelerants of any of E13 to E13.3.

E35. The kit of any of E33, E34, or E34.1, wherein the water-soluble matrix is molded into the cap or the container.

E36. The kit of any of E33 to E35, wherein the oxidizing agent is a percarbonate salt.

E36.1. The kit of any of E33 to E35, wherein the oxidizing agent is a perborate salt.

E37. A system for disposing of a pharmaceutical dosage form comprising a blender, water, and a mixture of an oxidizing agent, an optional organic peroxide accelerant, and an optional solubility enhancer.

E38. The system of E37, wherein the oxidizing agent, organic peroxide accelerant, and solubility enhancer are as defined in any of E6-E36.

I claim:

1. A method for disposing of a pharmaceutical dosage form comprising:
   contacting a pharmaceutical dosage form comprising an active pharmaceutical ingredient comprising one or more nitrogen atoms with an aqueous mixture comprising:
     one molar equivalent of an oxidizing agent selected from sodium perborate, sodium percarbonate, m-chloroperbenzoic acid, acetyl peroxide, benzoyl peroxide, or sodium hypochlorite; a ferrocene catalyst; and
     one or more organic peroxide accelerants selected from tetraacetylethylenediamine, nonanoyloxybenzene sulphonate, or (triethylamoniomethyl)benzoyl caprolactam chloride;
   releasing the active pharmaceutical ingredient from the pharmaceutical dosage form; and
   reacting the active pharmaceutical ingredient with the oxidizing agent and the organic peroxide accelerant for 10 to 20 minutes to oxidize the active pharmaceutical ingredient into a pharmacologically inactive product; wherein the contacting, releasing and reacting procedures are performed at room temperature.

2. The method of claim 1, wherein the active pharmaceutical ingredient is oxidized and dealkylated.

3. The method of claim 1, wherein the aqueous mixture further comprises one or more acids, bases, buffers, alcohols, surfactants, or detergents that enhances the release of the active pharmaceutical ingredient from the pharmaceutical dosage form.

4. The method of claim 1, wherein the active pharmaceutical ingredient comprises one or more of opioids, amphetamines, cocaine, benzodiazepine, or derivatives thereof.

5. The method of claim 1, wherein the active pharmaceutical ingredient comprises oxycodone, oxymorphone, hydromorphone, hydrocodone, fentanyl, tramadol, tapentadol, ethylmorphine, buprenorphine, pethidine, levorphanol, methadone, or dextropropoxyphene.

6. The method of claim 1, wherein the method further comprising releasing the oxidizing agent from a tablet, gel-cap, capsule, gel, or powder.

7. The method of claim 1, wherein the contacting the pharmaceutical dosage form with the aqueous mixture is performed in a pharmaceutical dosage form container.

8. The method of claim 7, further comprising releasing the oxidizing agent and organic peroxide accelerant from a compartment in the pharmaceutical dosage form container.

9. The method of claim 8, wherein the compartment is inside the cap of the pharmaceutical dosage form container.

10. The method of claim 1, wherein the aqueous mixture comprises:
- the one or more oxidizing agents;
- the one or more organic peroxide accelerants;
- a ferrocene catalyst;
- one or more acids, bases, buffers, alcohols, surfactants, or detergents; and
- water.

* * * * *